Figure 1:
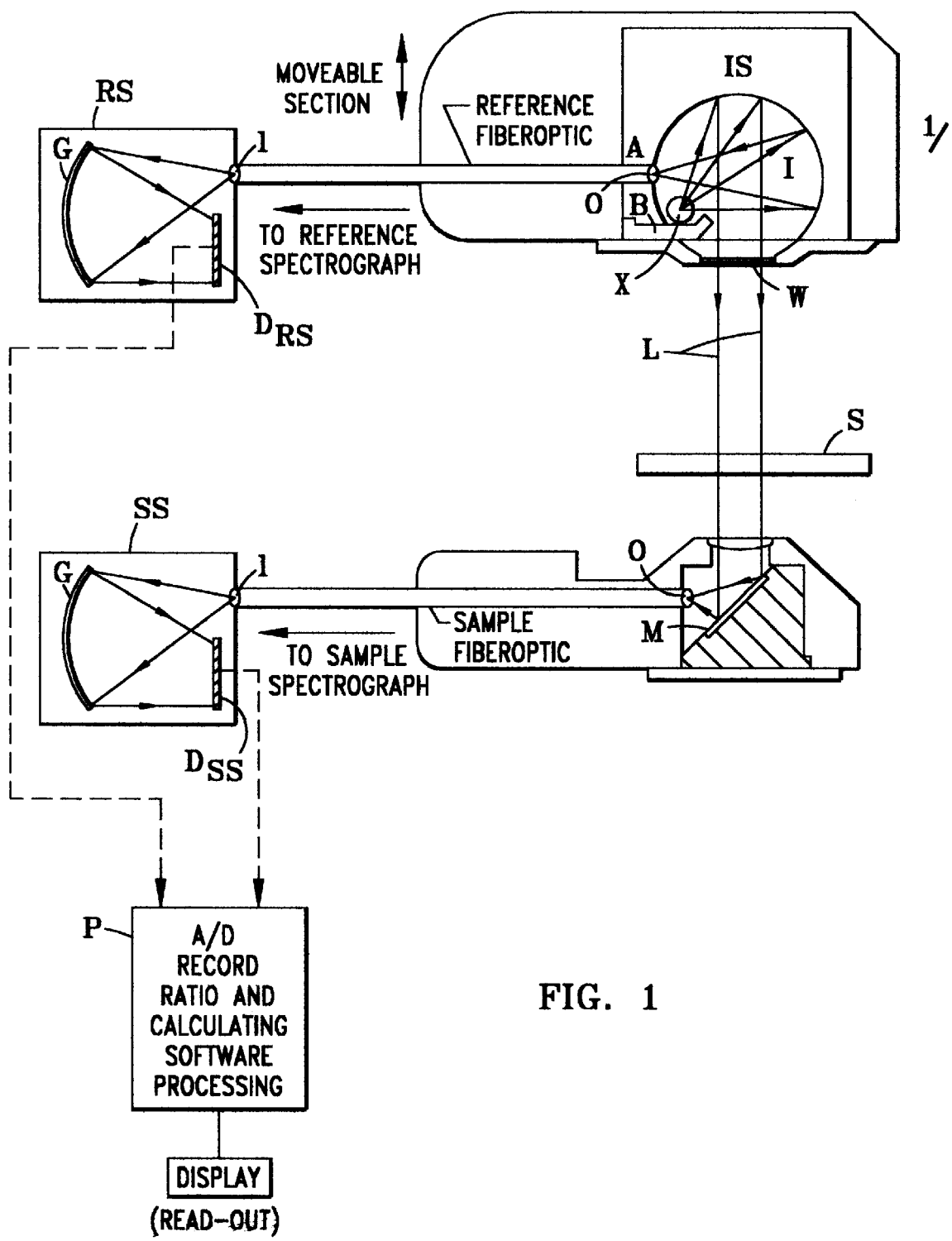

United States Patent [19]
Jablonski et al.

[11] Patent Number: 5,923,039
[45] Date of Patent: Jul. 13, 1999

[54] ULTRAVIOLET TRANSMITTANCE ANALYZING METHOD AND INSTRUMENT

[75] Inventors: Joseph Jablonski, Pembroke; Norman Carlson, Warner, both of N.H.

[73] Assignee: Labsphere, Inc., North Sutton, N.H.

[21] Appl. No.: 08/931,699

[22] Filed: Sep. 16, 1997

[51] Int. Cl.⁶ ................................................. G01N 21/33
[52] U.S. Cl. ..................... 250/373; 250/372; 250/504 R
[58] Field of Search ................................... 250/372, 373, 250/504 R, 228; 356/326

[56] References Cited

U.S. PATENT DOCUMENTS

| | | |
|---|---|---|
| 4,965,454 | 10/1990 | Yamauchi et al. ..................... 250/372 |
| 5,339,151 | 8/1994 | Shinn ..................................... 250/372 |
| 5,679,949 | 10/1997 | Task et al. ........................... 250/504 R |

*Primary Examiner*—Constantine Hannaher
*Assistant Examiner*—Darren M. Jiron
*Attorney, Agent, or Firm*—Rines and Rines

[57] ABSTRACT

An ultraviolet transmittance analyzer for fabrics, translucent packaging, sunscreen products and the like using an internally pulsed white-light illuminated integrating sphere, exiting sample and reference diffusely reflected beams, and applying them respectively to separate sample and reference spectrographs with light detector arrays.

23 Claims, 3 Drawing Sheets

```
SAMPLE:              SUNSCREEN SAMPLE B
OPERATOR:            MONA YUREK
CLIENT:              CAMELOT COSMETICS
COMMENT:             SAMPLE #2 OF 5
DATE:                13 NOV. 1996
TIME:                12:34 PM
WAVELENGTH RANGE:    280-400 nm

SPF      T(UVA)     T(UVB)
UNITS:               5         5          5
# OF SCANS:        4.391    32.03%     21.82%
MEAN:              0.707     4.255%     4.209%
STD:              16.10%    13.28%     19.28%
COV:               0.83
UVA RATIO:         ****     MAXIMUM
STAR CATEGORY

SCAN #   SPF              SCAN #   SPF
  1     3.302                7
  2     5.074                8
  3     4.095                9
  4     4.817               10
  5     4.671               11
  6                         12
```

```
WAVELENGTH    SCAN # 2
   280         31.81
   281         31.13
   282         30.569
   283         30.098
   284         29.674
   285         29.269
   286         28.85
   287         28.448
   288         28.041
   289         27.696
   290         27.384
```

ULTRAVIOLET TRANSMITTANCE ANALYZING METHOD AND INSTRUMENT

The present invention relates to the measurement of the transmission of ultraviolet light through diffusing materials such as fabrics, translucent packaging and similar materials, and ultraviolet light-protecting skin creams and the like, among other applications.

BACKGROUND OF THE INVENTION

The measurement of ultraviolet transmission is useful in a myriad of applications for determining the amount of degradation caused by ultraviolet rays to fabrics and similar articles, to products contained within translucent packaging materials therefor, including pharmaceutical product bottles or containers and the like, and also for ascertaining the degree of ultraviolet protection to the skin afforded by clothing and protective creams, including so-called sunscreen formulations.

In the past, such measurements have been made by striking the sample with ultraviolet light and collecting the light transmitted through the sample with an integrating sphere as, for example, of the type described in U.S. Pat. No. 5,537,203 of the common assignee of the present invention. The light is either provided by a scanning monochrometor, or a scanning, monochrometor is used to analyze the light after it passes into the sphere.

Limitations in such prior techniques, at least for the specific purposes of the present invention, as above summarized, include the relatively slow, several minute measurement time required of such scanning monochrometors, and the substitution errors exhibited in the integrating sphere measurements due to the presence of the sample on the sphere during its transmission measurement and the absence of the sample during the required reference beam scan measurement. In addition, fluorescent effects in the sample, common with commercial fabrics and other materials, cannot be satisfactorily dealt with in such monochrometors, though partially compensatory optical filters have been used. The steady irradiation required, moreover, can itself affect the sample, indeed, changing it in the very process of measurement.

The present invention, on the other hand, admirably overcomes all of these prior limitations and disadvantages through the use of a pulsed white light (xenon) lamp inside an integrating sphere and the use of two separate diode array spectrograph channels, with light collected in a single direction after it passes through the sample, and with one channel monitoring the inside of the sphere, and the other channel viewing the light transmitted through the sample.

OBJECTS OF INVENTION

The primary object of the invention, accordingly, is to provide a new and improved method of and instrument for such measurement of the transmission of ultraviolet light through diffusing materials that shall not be subject to the above-described and other limitations of prior techniques and apparatus, but that, to the contrary, enables rapid, few-second measurements, eliminates substitution errors, correctly deals with induced fluorescent effects, and provides for only brief exposure to the light source.

Other and further objects will be explained hereinafter and are more particularly delineated in the appended claims.

SUMMARY

In summary, from one of its broader viewpoints, the invention embraces an instrument for measuring and analyzing the ultraviolet transmittance of samples, having, in combination, a light-integrating sphere provided with an internal spherical wall for diffusely reflecting light from an internally positioned source, a pair of apertures spaced along the sphere for exiting reflections externally of the sphere along a corresponding pair of different paths, means for enabling the disposing of a sample in one path to pass some of the diffusely reflected light exiting the sphere through the corresponding aperture through the sample, and thereafter to direct the light to a sample spectrograph provided with a photodiode or other suitable detector array, means for directing other diffusely reflected light exiting the other aperture of the sphere along the other path to a reference spectrograph provided with a photodiode or other suitable detector array, and means for determining from the measurements of the photodiode or other detector arrays the ultraviolet transmittance of the sample.

Preferred and best mode designs and operational techniques will later be described in detail.

DRAWINGS

The invention will now be described with reference to the accompanying drawings, FIG. 1 of which is a combined transverse section and diagrammatic operational view of a preferred instrument constructed in accordance with the invention and adapted for measurements under its method of operation; and FIGS. 2A–C and FIGS. 3A–C are experimentally obtained performance values illustrating such operation for ultra-violet transmittance analysis of fabric and sunscreen samples, respectively.

PREFERRED EMBODIMENT(S) OF INVENTION

As shown in FIG. 1, the analyzer instrument of the invention is illustrated in the form of a rugged and convenient bench top instrument 1 adapted for quick and accurate measurement of the spectral transmittance of fabric, sunscreen or other samples inserted at S into the path of light L originating from a preferably pulsed white light xenon flashlamp X, optimized for UV emission, and mounted at baffle B within an integrating sphere IS (as of the type described in said patent), and diffusely reflecting white light from the entire inner surface walls of the sphere, utilizing the total energy from the xenon flashlamp for optimal signal-to-noise performance. The baffle B is shaped to prevent direct light from the flashlamp from exiting the later-described window aperture W in the sphere. The pulsing of the flashlamp, such as one to three pulses per scan at a flash pulse duration of, for example, approximately 10 microseconds for a measurement, illuminates the sample S only briefly during the measurement, minimizing any possible sample degradation from the exposure. The diffuse illumination geometry of the sphere, moreover, measures the transmittance from all angles and pathlengths through the sample S, with this design delivering exceptional wavelength stability and flash-to-flash repeatability.

As before stated, two separate preferably diode array spectrograph channels are employed in accordance with the invention: one, receiving light passing downwardly through the lower window aperture region W in the integrating, sphere IS and enabling viewing of the light L transmitted through the sample S and reflected from an inclined mirror M laterally along a fiberoptic sample signal path, so-labeled, shown horizontal in the lower section of the instrument, to a sample spectrograph SS, and the other, monitoring the illuminating light I inside of the sphere through a second aperture region A, shown 90° to the side, and along a horizontally extending reference fiberoptic path, so-labeled, in the upper section of the instrument 1, and passing rays to a reference spectrograph RS. The upper and lower instrument sections are preferably vertically relatively movable as shown.

Each spectrograph SS and RS impinges its input light rays upon a corresponding concave holographic diffraction grating G (for example, of the type manufactured by American Holographic Company of Fitchburg, Mass.) for detection by respective linear photodiode arrays $D_{SS}$ and $D_{RS}$, the diode arrays providing fast measurement in about five seconds or so. The sample-illuminating light is thus collected in a single direction after passing through the sample (for example, with a 10 mm sample beam diameter), the diffuse illumination/directional collection geometry being reciprocal to and equivalent to the more usual directional illumination/diffuse collection geometry.

The RS spectrograph monitoring of the inside of the sphere IS, furthermore, serves to correct for flash-to-flash variations in the xenon or similar source, and it also eliminates the before-described substitution error by providing simultaneous monitoring of the illuminating light I and the transmitted light L. By using white light, in addition, the instrument views induced fluorescence correctly Thus, all the before-described limitations in prior art measurements are admirably overcome with the analyzing technique and instrument design of the invention.

The efficiency of the dual diode array spectrometers, coupled with the pulsed xenon flash lamp utilization, as above described, enables reliable and repeatable measurement results in seconds, and appropriate instrument software can automatically calculate the average value for the UVB (280–315 nm), UVA (315–400 nm) and SPF rating (sun protective factor), either for the ultraviolet blocking ability of, for example, fabrics or the like, or the UVA to UVB ratio, in turn convertible to the sunscreen product so-called Boots Star Rating level. The application software, so-labeled, may include preprogrammed solar spectral irradiance and CIE erythermal action spectra to enable precise calculation of the SPF value of the sample multiple scans, averaged and viewed simultaneously in easy-to-read formats.

DESIGN CONCEPT AND DETAILS OF OPERATION

The flashlamp X inside the integrating sphere IS produces a broad spectrum in the UV, notably over the range of wavelengths covered by the spectrographs: 250 nm to 450 nm, with the total spectral radiant flux from the lamp being collected by the integrating sphere, illuminating the interior sphere walls as before explained. The spectral reflectance of the sphere walls creates a uniform spectral radiance which is viewed by each spectrograph. The spectral transmittance of the sample S is determined by the reduction in spectral radiance as viewed by the sample spectrograph SS.

While a xenon arc lamp with a quartz envelope is a good choice of a lamp in a UV spectrophotometer, however, the unwanted infrared emission of an arc lamp can thermally alter sample spectrophotometric properties. The desired UV emission, moreover, as previously alluded to, can also induce either temporary or permanent chemical changes in the sample properties due to the high energy photons in this spectral region. The use of a xenon flashlamp X, in accordance with the present invention, on the other hand, minimizes the exposure of the sample to instrument radiation.

The fast spectral data acquisition offered by a photodiode array spectrograph, SS-$D_{SS}$ and RS-$D_{RS}$, can capture a spectrum in a single flash. Since flashlamps are inherently non-repeatable in spectral distribution from flash to flash, especially when the spectral resolution is less than 10 nm, such use of a flashlamp, therefore, drives the need for the two spectrographs—the reference spectrograph RS being used primarily to measure the spectrum of each flash.

In actuality, the reference spectrograph RS serves a dual purpose in the integrating sphere-spectrophotometer system of the invention. The spectral radiance of the sphere wall is a function of both the flux from the flashlamp and the reflectance of the sphere wall. Samples S placed at the opening W in the integrating sphere wall and their tangential surface reflectance influences the average sphere wall reflectance. This is classically known as integrating sphere substitution error, earlier mentioned. The substitution of different samples of various reflectance values alters the measured spectrophotometric scale, either transmittance or reflectance. A direct measurement must, accordingly, be made of the sphere wall radiance with each sample present in order to correct the error. While it is not necessary to use a separate spectrograph, such is, however, precipitated, in accordance with the invention, by the use of a flashlamp.

As before explained, each spectrograph has of a fiberoptic input. The spectrograph in the sample viewing path also includes a lens, so-labeled in FIG. 1, to control the area of view on the samples. The fiberoptic cable consists of a bundle of fibers preferably arranged substantially in a circle on the radiation input end, as schematically shown at O in FIG. 1. On the spectrograph end, the fibers are arranged in a line to simulate a rectangular slit. Inside each spectrograph, the concave holographic diffraction grating both disperses the broad UV spectrum and images the entrance slit into the corresponding linear array of silicon photodiodes $D_{SS}$, $D_{RS}$, which include 128 individual, rectangular elements of pixels as an illustration. Each pixel, therefore, captures a narrow band of UV radiation, roughly equivalent to the product of the linear dispersion of the diffraction gyrating and the pixel width. The following describes how the radiation incident on the pixels of both spectrograph diode arrays is used to determine the UV spectral transmittance of a sample S.

Ratiometric Measurement

An important aspect of spectrophotometer design is the prediction of the signal-to-noise ratio which includes the radiometry of the previously described system. This would estimate the photon flux incident on each photodiode array within the spectrograph and predict the generation of electrons via the photoelectric effect and the quantum efficiency of the silicon diodes. However, in terms of measuring spectral transmittance, the photo flux is incidental. The measurement is rather performed in terms of the ratio of the relative photon flux between each spectrograph which is represented by the relative signal measured for each photodiode array by the associated conventional electronic means.

Raw Spectrograph Data

Since there is a "dark signal" from a photodiode array without incident radiant flux due to a random or thermal flow of electrons, the signal of the flashlamp must be corrected by measuring and subtracting the dark signal. The spectrograph scans (signal from each pixel) are recorded in units of ADC counts from an analog-to-digital converter) vs. Pixel (p) The dark scan for each spectrograph is recorded before the flashlamp is activated.

By the definitions of Table 1, below.

TABLE 1

| Flashlamp Status | Spectrograph Scan |
|---|---|
| on | L(p) |
| off | D(p) | the net, dark corrected signals are:

$$X(p) = L_1(p) - D(p) \qquad 1$$

Conversion from Pixel to Wavelength Space

The net spectrograph data, X(p), is converted into wavelength space, X(λ), using a $3^{rd}$ order polynomial.

$$\lambda = a + bp + cp^2 + dp^3 \qquad 2$$

The coefficients a–d are derived as a best fit using the method of least squares from locating the image of 5 emission lines in pixel space produced by a low pressure mercury lamp. Sub pixel resolution is achieved by curve-fitting the broadened image of each spectral line to find its true center. An example of the calibration for one spectrograph follows:

TABLE 2

| actual λ | pixel | fit | coefficients | interpolated λ | error |
|---|---|---|---|---|---|
| 253.7 | 4.6 | a | 246.23 | 253.7 | 0.0 |
| 313.2 | 41.3 | b | 1.6351 | 313.1 | −0.1 |
| 365.0 | 73.6 | c | −4.034E-04 | 365.1 | +0.1 |
| 404.7 | 98.1 | d | 1.906E-06 | 404.6 | −0.1 |
| 435.8 | 117.5 | | | 435.8 | 0.0 |

The 128 pixels are spaced by approximately 1.5 nm. The ADC counts are then interpolated to a 1 nm spacing using multiple two point linear interpolations. This produces 201 data points for a wavelength range of 250 nm–450 nm for each spectrograph.

Blank Scan (100% T calibration)

The blank scan (no sample present) produces, in wavelength space, a baseline data file which is the ratio of the net, dark corrected counts on the two diode arrays (sample and reference spectrographs SS and RS).

Sample Transmittance

After a blank scan is recorded, the sample S is placed into its beam path, reducing the signal recorded by the sample spectrograph SS by an amount proportional to its transmittance. The sample spectral transmittance T is the ratio of the net counts on both diode arrays divided by the baseline file from the blank scan:

$$T_2 = \frac{X_3(\lambda)}{X_1(\lambda)} \div B \qquad \text{Eq.4}$$

Referring to FIG. 1, this is schematically illustrated by the processing blocks P.

Figures 2A, 2B, 2C:
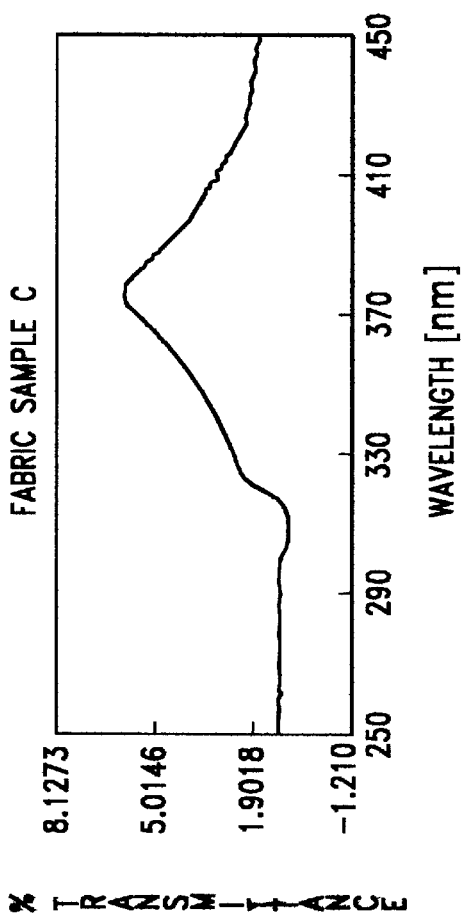

FIGS. 2A, B and C illustrate, respectively, a graph of transmittance versus UV wavelength obtained with the instrument of FIG. 1 for a fabric sample, a corresponding wavelength-scan data table, and a corresponding software-derived SPF Rating Report.

Figures 3A, 3B, 3C:
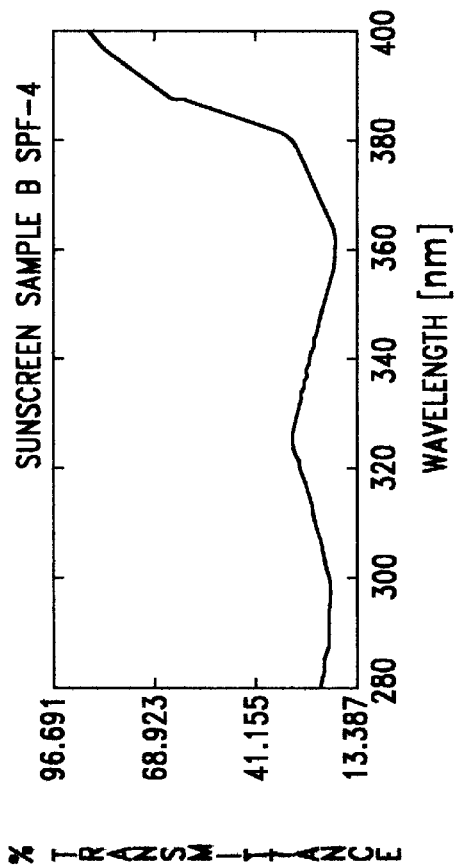

FIGS. 3A, B and C are similar to FIGS. 2A, B and C but report results obtained for a sunscreen product sample, using the term SPF for in vitro tests (usually referred to as UPF—ultraviolet protective factor, to distinguish from SPF determined by in vivo tests).

As before stated, other white-light-producing flashlamps may also be used, as may other detectors than photodiodes, such as CCD's and further modifications will also occur to those skilled in this art, and such are considered to fall within the spirit and scope of the invention as defined in the appended claims.

What is claimed is:

1. An instrument for measuring and analyzing ultraviolet transmittance of samples, having, in combination, a light-integrating sphere provided with an internal spherical wall for diffusely reflecting light from an internally positioned light source; a pair of apertures spaced along the sphere for exiting reflections externally of the sphere along a corresponding pair of different paths; means for enabling the disposing of a sample in one path to pass some of the diffusely reflected light exiting the sphere through the corresponding aperture through the sample, and thereafter to direct the light to a sample spectrograph provided with a detector array, means for directing other diffusely reflected light exiting the other aperture of the sphere along the other path to a reference spectrograph provided with a detector array, and means for determining from the measurements of the detector arrays, the ultraviolet transmittance of the sample.

2. An instrument as claimed in claim 1 and in which the light source is a source of white light.

3. An instrument as claimed in claim 2 and in which the source comprises a pulsed xenon flashlamp.

4. Apparatus as claimed in claim 2 and in which the flashed white light contains a broad spectrum in the UV over a range of wavelengths of about 250 nm to 450 nm.

5. Apparatus as claimed in claim 2 and in which the measurement of the UV transmittance is effected by a circuit connected for determining the ratio of the relative signals measured by spectrograph light detector arrays with a sample present, divided by the ratio measured with no sample present.

6. An instrument as claimed in claim 1 and in which said corresponding aperture is a window disposed at the bottom of the sphere to exit light downwardly through the sample.

7. An instrument as claimed in claim 6 and in which there is provided an inclined mirror for directing the light that has passed through the sample laterally along a fiberoptic channel to the sample spectrograph.

8. An instrument as claimed in claim 1 and in which said other aperture is disposed in a side of the sphere and is provided with a laterally extending fiberoptic channel to the reference spectrograph.

9. An instrument as claimed in claim 1 and in which each of the means for directing light to the sample spectrograph and to the reference spectrograph comprises a fiberoptic channel.

10. An instrument as claimed in claim 9 wherein the fiberoptic channel to the sample spectrograph receives the light exiting a bottom aperture of the sphere and passed through the sample after reflection from an inclined mirror.

11. An instrument as claimed in claim 10 wherein the fiberoptic channel to the reference spectrograph receives the light at said other aperture disposed on a side of the sphere.

12. An instrument as claimed in claim 11 wherein the said other aperture is disposed substantially 90° displaced along the sphere from the bottom aperture, and the fiberoptic channels extend parallelly in the instrument, substantially horizontally.

13. An instrument as claimed in claim 12 wherein the integrating sphere-reference fiberoptic channel assembly is disposed in an upper section of the instrument relatively movable upward and downward with respect to a lower instrument section containing the mirror-sample fiberoptical channel assembly.

14. Apparatus as claimed in claim 9 and in which each fiber optic channel comprises a bundle of optical fibers arranged in substantially circular cross-section at their ends receiving light passed through the respective apertures, and in a line at the respective spectrographs.

15. An instrument as claimed in claim 1 wherein the light source is a pulsed flashlamp positioned at an internal wall section of the sphere between said other and said corresponding apertures, and provided with a baffle to prevent direct light transmission from the flashlamp through said corresponding aperture.

16. An instrument as claimed in claim 1 wherein the flashlamp is a white light source such as a xenon flashlamp, and is pulsed.

17. A method of measuring and analyzing ultraviolet transmittance of samples, that comprises, simultaneously exiting diffusedly reflected internally generated light from the internal surface of an integrating sphere through a pair of spaced apertures in the sphere and along a corresponding pair of different paths; inserting a sample in one path and directing the light from its corresponding aperture through the sample and thence to a sample spectrograph having a light detector, directing the light from the other aperture along the other path to a reference spectrograph having a light detector; and determining from the photodetector measurements, the ultraviolet transmittance of the sample.

18. A method as claimed in claim 17 and in which the light generated internally of the sphere is provided by pulsing a white light flashlamp positioned therewithin.

19. A method as claimed in claim 18 and in which light is conducted in each path along fiber optic channels.

20. A method as claimed in claim 18 and in which a sample, of fabric and protective packaging, is inserted into said one path, and a spectral transmittance value is obtained upon pulsing the flashlamp, and is then converted to a sun protective factor for the sample.

21. A method as claimed in claim 18 and in which a sample of sunscreen product is inserted into said one path and a spectral transmittance value is obtained upon pulsing the flashlamp, and is then converted to a sun protective factor for the sample.

22. A method as claimed in claim 18 wherein the UV transmittance measurement is effected by calculating the ratio of the relative signals measured by spectrograph photodiode arrays with a sample present divided by such ratio with no sample present.

23. A method as claimed in claim 22 wherein the flashlamp is flashed after the measurement with no sample.

* * * * *